United States Patent [19]

Fukuda et al.

[11] 4,104,282

[45] Aug. 1, 1978

[54] NOVEL 3-(OXYGENATED ALKYL)-1,9-DIHYDROXY AND 1-HYDROXY-9-KETO DIBENZO[b,d]PYRANS

[75] Inventors: David S. Fukuda, Brownsburg; Bernard J. Abbott, Greenwood; Robert A. Archer, Indianapolis, all of Ind.

[73] Assignee: Eli Lilly and Company, Indianapolis, Ind.

[21] Appl. No.: 822,467

[22] Filed: Aug. 8, 1977

Related U.S. Application Data

[62] Division of Ser. No. 694,512, Jun. 9, 1976, Pat. No. 4,064,009.

[51] Int. Cl.$^2$ .......................................... C07D 311/78
[52] U.S. Cl. ................................. 260/345.3; 424/283
[58] Field of Search ...................................... 260/345.3

[56] References Cited

PUBLICATIONS

Fahrenholtz et al., JACS, 88, 2078 (1966).

*Primary Examiner*—Nicky Chan
*Attorney, Agent, or Firm*—James L. Rowe; Everet F. Smith

[57] ABSTRACT

1-Hydroxy-9-keto-3-alkyl-dibenzo[b,d]pyrans or 1,9-dihydroxy-3-alkyl-dibenzo[b,d]pyrans are oxygenated on the penultimate carbon of the alkyl side chain by fermentation with a strain of the micro-organism *Bacillus cereus.*

5 Claims, No Drawings

NOVEL 3-(OXYGENATED ALKYL)-1,9-DIHYDROXY AND 1-HYDROXY-9-KETO DIBENZO[b,d]PYRANS

This is a division of application Ser. No. 694,512, filed Jun. 9, 1976, now U.S. Pat. 4,064,009.

BACKGROUND OF THE INVENTION

U.S. Pat. Nos. 3,822,188, 3,808,234, and 3,864,492 all to Fager et al. disclose the fermentation of $\Delta^9$-THC (1-hydroxy-3-n-pentyl-6,6,9-trimethyl-6a,7,10,10a-tetrahydrodibenzo[b,d]pyran) with such micro-organisms as *Cunninghamella blakesleeana, Streptomyces viridoilavus, Mucor parasiticus, Aspergillus fonsecaeus,* etc. to produce the corresponding 4'-hydroxy derivatives; i.e., compounds in which the n-pentyl side-chain is oxidized on its penultimate carbon by the action of the microorganism. The compounds thus produced are said to be anti-depressants. Vidic et al., U.S. Pat. No. 3,897,306, oxidize an isomer ($\Delta^8$-THC) with *Streptomyces lavendulae* or with *Peliculiaria filamentosa* to produce a quite different compound in which the C-7 carbon is hydroxylated to yield a 7-hydroxy-$\Delta^8$-THC derivative. Robertson, et al., *Biomedical Mass Spectrometry,* 1975(2) 266–271 find that exposure of $\Delta^9$-THC, $\Delta^8$-THC, cannabinol, and cannabidiol to the fungus *Syncephalastrum racemasum* yields products which carry a hydroxyl group on the penultimate carbon atoms.

A series of 1-hydroxy-3-alkyl-6,6a,7,8,10,10a-hexahydro-9H-dibenzo[b,d]pyran-9-ones have been found by Archer to be useful as anti-depressant, anti-anxiety, sedative, and analgesic drugs—see U.S. Pat. No. 3,928,598. Compounds of this structure were first synthesized by Fahrenholtz, et al., *J. Am. Chem. Soc.,* 88 2078 (1966), 89, 5934 (1967), as intermediates for the preparation of $\Delta^8$- or $\Delta^9$-THC. (See also U.S. Pat. No. 3,507,885 and U.S. Pat. No. 3,636,058). The same group of $\Delta^8$- and $\Delta^9$-THC compounds are disclosed by Petrzilka in U.S. Pat. No. 3,873,576.

SUMMARY OF THE INVENTION

This invention provides a novel group of sidechain oxygenated dibenzo[b,d]pyrans of the following formula:

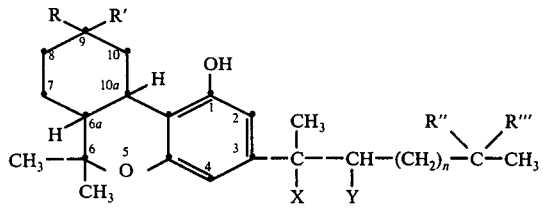

wherein X and Y are either both hydrogen or one is hydrogen and the other methyl;
wherein, when taken singly, one of the pair R and R' and one of the pair R" and R''' is H and the other is OH and, when taken together, the pair R and R' and the pair R" and R''' form the oxygen of a ketone group; and wherein *n* is 1, 2, 3 or 4.

The above compounds are prepared by subjecting a compound of the following formula:

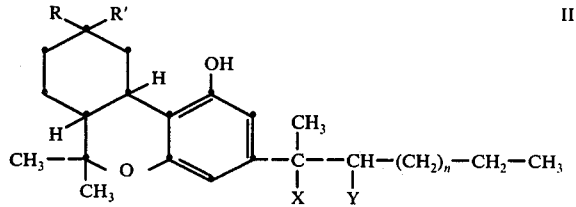

wherein R, R', X, Y and *n* have the same meaning as hereinabove, to the oxygenating activity of a microorganism of the species *Bacillus cereus.* The oxygenating action of the *Bacillus cereus* species upon the dibenzopyran-1-ol-9-ones or dibenzo pyran-1,9-diols substrates can take place under standard submerged culture fermentation conditions, or the growing micro-organism cells can be harvested, resuspended, and the substrate added to the resulting suspension.

The novel products according to Formula I above produced during the fermentation were isolated by standard extraction procedures and were purified by high performance liquid chromatography and/or preparative thin-layer chromatography. The structures were determined by NMR spectroscopy, mass spectroscopy, UV spectroscopy and infra-red spectroscopy. Compounds preparable by the above procedure include the following:

From trans-1-hydroxy-3-(1',2'-dimethylheptyl)-6,6-dimethyl-6,6a,7,8,10,10a-hexahydro-9H-dibenzo[b,d]pyran-9-one.
 a. trans-1,6',9-trihydroxy-3-(1',2'-dimethylheptyl)-6,6-dimethyl-6,6a,7,8,10,10a-hexahydro-9H-dibenzo[b,d]pyran.
 b. trans-1,9-dihydroxy-3-(1',2'-dimethylheptyl)-6,6-dimethyl-6,6a,7,8,10,10a-hexahydro-9H-dibenzo[b,d]pyran-6'-one.
 c. trans-1,6'-dihydroxy-3-(1',2'-dimethylheptyl)-6,6-dimethyl-6,6a,7,8,10,10a-hexahydro-9H-dibenzo[b,d]pyran-9-one.
 d. (±)-trans-1-hydroxy-3-(1',2'-dimethylheptyl)-6,6-dimethyl)-6,6a,7,8,10,10a-hexahydro-9H-dibenzo[b,d]pyran-6',9-dione.

From trans-1-hydroxy-3-(1',1'-dimethyloctyl)-6,6-dimethyl-6,6a,7,8,10,10a-hexahydro-9H-dibenzo[b,d]pyran-9-one.
 a. trans-1,7',9-trihydroxy-3-(1',1'-dimethyloctyl)-6,6-dimethyl-6,6a,7,8,10,10a-hexahydro-9H-dibenzo-[b,d]pyran.
 b. trans-1,9-dihydroxy-3-(1',1'-dimethyloctyl)-6,6-dimethyl-6,6a,7,8,10,10a-hexahydro-9H-dibenzo[b,d]pyran-7'-one.
 c. trans-1,7'-dihydroxy-3-(1',1'-dimethyloctyl)-6,6-dimethyl-6,6a,7,8,10,10a-hexahydro-9H-dibenzo[b,d]pyran-9-one.
 d (±)-trans-1-hydroxy-3-(1',1'-dimethyloctyl)-6,6-dimethyl-6,6a,7,8,10,10a-hexahydro-9H-dibenzo[b,d]pyran-7',9-dione.

From cis-1-hydroxy-3-(1',1'-dimethylheptyl)-6,6-dimethyl-6,6a,7,8,10,10a-hexahydro-9H-dibenzo[b,d]pyran-9-one.
 a. cis-1,6',9-trihydroxy-3-(1',1'-dimethylheptyl)-6,6a,7,8,10,10a-hexahydro-9H-dibenzo[b,d]pyran.
 b. cis-1,6'-dihydroxy-3-(1',1'-dimethylheptyl)-6,6a,7,8,10,10a-hexahydro-9H-dibenzo[b,d]pyran-9-one.
 c. cis-1,9-dihydroxy-3-(1',1'-dimethylheptyl)-6,6-dimethyl-6,6a,7,8,10,10a-hexahydro-9H-dibenzo[b,d]pyran-6'-one.

d. (±) cis-1-hydroxy-3-(1',1'-dimethylheptyl)-6,6-dimethyl-6,6a,7,8,10,10a-hexahydro-9H-dibenzo[b,d]pyran-6',9-dione.

From trans-1-hydroxy-3-(1',1'-dimethylpentyl)-6,6-dimethyl-6,6a,7,8,10,10a-hexahydro-9H-dibenzo[b,d]pyran-9-one.

a. trans-1,4',9-trihydroxy-3-(1',1'-dimethylpentyl)-6,6-dimethyl-6,6a,7,8,10,10a-hexahydro-9H-dibenzo[b,d]pyran.

b. trans-1,9-dihydroxy-3-(1',1'-dimethylpentyl)-6,6-dimethyl-6,6a,7,8,10,10a-hexahydro-9H-dibenzo[b,d]pyran-4'-one.

c. trans-1,4'-dihydroxy-3-(1',1'-dimethylpentyl)-6,6-dimethyl-6,6a,7,8,10,10a-hexahydro-9H-dibenzo[b,d]pyran-9-one.

d. (±)-trans-1-hydroxy-3-(1',1'-dimethylpentyl)-6,6-dimethyl-6,6a,7,8,10,10a-hexahydro-9H-dibenzo[b,d]pyran-4',9-dione.

Other compounds coming within the scope of Formula I above include:

cis-1,5'-dihydroxy-1',1',2',6,6-pentamethyl-3-hexyl-6,6a,7,8,10,10a-hexahydro-9H-dibenzo[b,d]pyran-9-one.

cis-1',2',6,6-tetramethyl-3-hexyl-6,6a,7,8,10,10a-hexahydro-9H-dibenzo[b,d]pyran-1,5',9-triol.

cis-1',2',6,6-tetramethyl-3-pentyl-6,6a,7,8,10,10a-hexahydro-9H-dibenzo[b,d]pyran-1,4',9-triol.

cis-1',2',6,6-tetramethyl-3-pentyl-6,6a,7,8,10,10a-hexahydro-9H-dibenzo[b,d]pyran-1,4'-diol-9-one and the like.

Compounds according to Formulas I or II above contain asymmetric centers at 6a, and 10a and at 9 when one or R or R' is hydroxyl and the other is hydrogen. In addition, there may be asymmetric centers in the side-chain alkyl group as, for example, when R' is 1,2-dimethylheptyl, two asymmetric centers are present in the side-chain at $C_1'$ and $C_2'$. The Fahrenholtz synthetic procedure described above in which the double bond isomerizes from the $\Delta^{6a(10a)}$ position to the $\Delta^{10(10a)}$ position produces a racemate in which $C_{6a}$ is asymmetric, the hydrogen being either above or below the plane of the dibenzopyran fused-ring system. Hydrogenation of the $\Delta^{10(10a)}$ double bond with, for example, an active metal in liquid ammonia produces a second asymmetric center at $C_{10a}$, but the hydrogen which adds to this carbon under the hydrogenation or reduction conditions will usually take the more favorable trans configuration relative to the hydrogen at $C_{6a}$ with a lesser quantity of compound of the cis configuration being produced. Reduction of the ketone group at $C_9$ yields a mixture of isomers in which the hydroxyl group is in the axial (9α) or equatorial (9β) configuration. Thus a compound in which the side chain contains no asymmetric centers, as for example 1,9-dihydroxy-3-(1',1'-dimethylheptyl)-6,6-dimethyl-6,6a,7,8,10,10a-hexahydro-6H-dibenzo[b,d]pyran, will occur as four racemates or racemic pairs to give a total of 8 stereoisomers. Compounds such as 1,9-dihydroxy-3-(1',2'-dimethylheptyl)-6,6-dimethyl-6,6a,7,8,10,10a-hexahydro-6H-dibenzo[b,d]pyran containing two additional asymmetric centers in the side chain will have a total of five asymmetric centers, those at 6a,9,10a and at $C_1'$ and $C_2'$ in the side chain, yielding altogether 32 possible isomers occuring as 16 racemates.

Compounds having a ketone group at $C_9$ will, of course, have one less asymmetric center. For example, 1-hydroxy-3-(1',1'-dimethylheptyl)-6,6-dimethyl-6,6a,7,8,10,10a-hexahydro-6H-dibenzo[b,d]pyran-9-one would occur as 4 stereoisomers instead of 8 with the 9-hydroxy analogs.

In addition, the process of this invention whereby the penultimate carbon atom of the alkyl side chain is hydroxylated produces an additional asymmetric carbon. This hydroxylation is believed to be stereoselective; i.e., one of two possible isomers is predominantly, if not virtually entirely, produced.

If the end product of the process of this invention is a side-chain ketone, there would be no additional asymmetric carbon and the number of stereoisomers unchanged from the number present in the substrate. The fermentation processes of this invention can also produce an asymmetric center at $C_9$ by reduction of a $C_9$ ketone employed as a substrate thereby increasing by one the number of asymmetric carbons. Again, this reduction is believed to be predominately stereospecific in that only one of the $C_9$ hydroxy isomers is produced; namely the 9S hydroxy isomer.

The compounds of this invention according to Formula I above are prepared as follows:

A lyophilized culture of *Bacillus cereus,* NRRL B-8172 is grown in a vegetative medium containing glucose, minerals, and yeast extract plus other ingredients. The culture is then transferred to a larger flask containing the same growth medium as before, and the organism is again incubated for a period of from one to two days. The chosen substrate can be added to the culture at this point or a cell suspension can be prepared by harvesting the cells from the growth medium and resuspending them in sterile buffer. The substrate is usually added as an ethanol solution and the fermentation carried on for a period of from 4 to 8 days. Any conversion products plus residual starting material are recovered by extracting the culture medium before or after filtration of the cells with a water immiscible solvent such as ethyl acetate. The organic extracts thus obtained are combined, washed with buffer, dried, filtered and then concentrated to dryness in vacuo. The products of the fermentation isolated in this residue are then separated by column chromatography.

Alternatively, the oxidation-reduction enzyme systems present in the cells can be isolated by lysing the cells, removing cell debris by filtration and collecting the isolated enzymes in the filtrate. As before, the substrate is added to the conversion system, in this case an isolated enzyme system, in proper concentrations and the reaction mixture shaken until a substantial amount of products according to Formula I above are formed.

This invention is more fully illustrated by the following specific example.

EXAMPLE

A soil isolate designated as *Bacillus cereus* NRRL B-8172 (A36659) was grown for 48–96 hours on a slant culture at a temperature in the range of 25°–30° C. using the following medium: Beef extract 1.5 g.; peptone 6.0 g.; yeast extract, 3.0 g.; agar, 20 g.; deionized water, 1 liter. The medium was autoclaved for 15 minutes at 121° C. (15 psi) prior to use. The culture was maintained on these slants at 4° C. The cells from 48–96 hour old slant culture were then lyophilized and stored at 4° C. The lyophilized cells were used to inoculate a flask of the following medium:

| | | |
|---|---|---|
| Glucose | 30 | g. |
| Yeast extract | 1.0 | g. |
| $(NH_4)_2SO_4$ | 10 | g. |

| | | |
|---|---|---|
| Na$_2$SO$_4$ | 0.5 | g. |
| K$_2$HPO$_4$ | 5.0 | g. |
| MgSO$_4$.7 H$_2$O | 0.4 | g. |
| FeSO$_4$.7 H$_2$O | 0.02 | g. |
| MnSO$_4$.4 H$_2$O | 0.02 | g. |
| NaCl | 0.02 | g. |
| H$_3$BO$_3$ | 0.5 | mg. |
| CuSO$_4$.5 H$_2$O | 0.04 | mg. |
| NaMoO$_4$.2 H$_2$O | 0.2 | mg. |
| ZnSO$_4$.7 H$_2$O | 8.0 | mg. |
| CaCl$_2$ | 0.05 | mg. |
| CoCl$_2$.6 H$_2$O | 0.2 | mg. |
| Deionized H$_2$O | 1.0 | l. |

The pH of the medium was adjusted to 7.0 with concentrated aqueous hydrochloric acid, and was dispensed in 50 or 100 ml. portions into 250 or 500 ml. erlenmeyer flasks respectively and each flask stoppered with a cotton plug. Each erlenmeyer flask containing medium was autoclaved as before. The autoclaved flasks were then inoculated. After inoculation with a lyophilized culture of NRRL B-8172 the culture flask was incubated at 30° C. on a rotary shaker (250 rpm 2.5 inch stroke) for 24-48 hours.

Cells were harvested from the above fermentations by centrifugation at 2300 rpm for 20-30 minutes at 4° C. The supernatant was separated by decantation, and the packed cells were washed with 0.1 M phosphate buffer at pH 6-7. The washed cells were then resuspended in a small volume buffer at pH=7.0, or a similar buffer containing 3 percent glucose. The resulting suspension was divided into 100 ml. to 125 ml. portions in sterile 500 ml. erlenmeyer flasks. 80 mg. of dl-trans-1-hydroxy-3-(1',1'-dimethylheptyl)-6',6-dimethyl-6,6a,7,8,10,10a-hexahydro-9H-dibenzo[b,d]pyran-9-one dissolved in 1.5 ml. of ethanol were added to each flask of cell suspension. After addition, the culture was further incubated for from 4-8 days. The incubated flasks were combined, and the combined cells and medium extracted four times, each time with ½ volume of ethyl acetate. The ethyl acetate extracts were combined, washed twice with one-tenth volume of water, dried, and the ethyl acetate therefrom removed by evaporation in vacuo. The resulting residue contained unmodified starting ketone plus a mixture of five fermentation-induced oxidation products of the starting ketone. The residue was subjected to high pressure liquid chromatography using a Merck silica gel 60 prepack column, equilibrated in chloroform under 2-6 psi of nitrogen. The residue was disolved in a small volume of chloroform and injected into this column which was chromatographed batch wise with solvent mixtures containing increasing concentrations of ethyl acetate. Column fractions shown to contain the same conversion product of the ketone substrate on TLC were pooled. The conversion product contained therein was further purified by preparative thin-layer chromatography as follows; the residual material obtained by evaporation of the pooled fractions to dryness was dissolved in ethyl acetate. The ethyl acetate solution was spotted on a silica gel thinlayer plate using 15-20 mg. sample per plate. The plates were developed in a 1:1 benzene:ethyl acetate solvent system, air-dried, and observed under ultra-violet light to mark the areas of the conversion product. These areas were eluted with chloroform and ethyl acetate to yield purified products.

The following are further typical runs made in accordance with the above procedure.

RUN I

Substrate: dl-trans-1-hydroxy-3-(1',1'-dimethylheptyl)-6,6-dimethyl-6,6a,7,8,10,10a-hexahydro-9H-dibenzo[b,d]pyran-9-one
Amount: 160 mg.
Incubation Time: 5 days
Separation: Chromatography over Silica gel
Conversion:

| Products | R$_f$ | Eluting Solvent | Weight |
|---|---|---|---|
| A | .500 | CHCl$_3$ | 5.5 mg. |
| C | .232 | CHCl$_3$, 2% EtOAc-98% CHCl$_3$ | 10.1 mg. |
| D | 179 | 10% EtOAc—90% CHCl$_3$ | 17.1 mg. |

Substrate and dl-trans-1,9-dihydroxy-3-(1',1'-dimethylheptyl)-6,6-dimethyl-6,6a,7,8,10,10a-hexahydro-9H-dibenzo[b,d]pyran-(6aR,10aR,9R isomer-reduction product of 9-keto group to an α-hydroxyl) were also isolated. Compounds A, C and D were isolated as yellow oils.

RUN II

Substrate: Same as I
Amount: 320 mg.
Incubation Time: 5 days
Separation: Same as I
Conversion:

Products

A, C, D — See I
B, R$_f$— 0.348, eluted with CHCl$_3$, 17.5 mg.

RUN III

Substrate: Same as I
Amount: 800 mg.
Incubation Time: 5 days
Separation: Same as I
Conversion:

Products

A, B, C, D
Also a quantity of 1,9-dihydroxy derivative, reduction product of the substrate.

COMPOUND A (±)-trans-3-(1',1'-Dimethylheptyl)-6,6a,7,8,10,10a-hexahydro-1-hydroxy-6,6-dimethyl-9H-dibenzo[b,d]pyran-6',9-dione UV(EtOH) $\lambda_{max}$ 208, 230 (shoulder) and 280 nm (ε=38000, 10000, and 200); ir (CHCl$_3$) 3.04 (OH) and 5.88μ (C=O); $^1$H NMR (CDCl$_3$) δ6.77 (s, 1H, exchanges with D$_2$O), 6.34, 6.30 (2d, 1H each, J=2Hz, H$_2$ and H$_4$), 4.08 (broad d, 1H, J=14Hz, H$_{10\alpha}$), 3.03-1.02 (30H) especially 2.35 (t, 2H, J=7Hz, H$_5$'), 2.07 (s, 3H, CH$_3$C=O), 1.47 (s, 3H, 6β-CH$_3$), 1.20 (s, 6H, M gem di-CH$_3$'s), and 1.11 ppm (s, 3H, 6α-CH$_3$); an exact mass determination gave m/e 386.2461 (calcd for C$_{24}$H$_{34}$O$_4$, 386.2457).

COMPOUND B (+)-trans-3-(1',1'-Dimethylheptyl)-6,6a,7,8,10,10a-hexahydro-1,6'-dihydroxy-6,6-dimethyl-9H-dibenzo[b,d]pyran-9-one UV(EtOH) $\lambda_{max}$ 207, 225 (shoulder), and 280 nm ($\epsilon$ = 16800, 4200, and 80); ir (CHCl$_3$) 3.03 (OH) and 5.90$\mu$ (C=O); $^1$H NMR (CDCl$_3$) $\delta$ 6.34 (s, 2H, H$_2$ and H$_4$), 4.08 (broad d, 1H, J=14Hz, H$_{10a}$), 3.74 (m, 1H, H$_6$'), 3.02–1.02 (32H) especially 1.47 (s, 3H, 6$\beta$-CH$_3$), 1.20 (s, 6H, gem di-CH$_3$'s), 1.15 (d, 3H, J=6Hz, CH$_3$C—OH), and 1.11 ppm (s, 3H, 6$\alpha$-CH$_3$); $[\alpha]^{25}$D + 46.3° (C$_3$, CHCl$_3$); and exact mass determination gave m/e 388.2614 (calcd for C$_{24}$H$_{36}$O$_4$, 388.2613).

COMPOUND C trans-3-(1',1'-Dimethylheptyl)-6,6a,7,8,10,10a-hexahydro-1,9-dihydroxy-6,6-dimethyl-9H-dibenzo[b,d]pyran-6'-one UV(EtOH) $\lambda_{max}$ 208, 227 (shoulder), and 280 nm ($\epsilon$ = 19000, 4600, and 80); ir (CHCl$_3$) 2.98 (OH) and 5.88$\mu$ (C=O); $^1$H NMR (CDCl$_3$) $\delta$ 6.34, 6.28 (2d, 1H each, J=2Hz, H$_2$ and H$_4$); 4.29 (broad s, 1H, H$_9$ equatorial), 3.27 (broad d, 1H, J=15Hz, H$_{10}$equatorial), 3.0–1.02 (32H) especially 2.96 (broad s, 1H, H$_{10a}$), 2.37 (t, 3H, CH$_2$—C=O), 2.08 (s, 3H, CH$_3$C=O), 1.39 (s, 3H, 6$\beta$-CH$_3$), 1.19 (s, 6H, gem di-CH$_3$'s), and 1.06 ppm (s, 3H, 6$\alpha$-CH$_3$); an exact mass determination gave m/e 388.2614 (calcd for C$_{24}$H$_{36}$O$_4$, 388.2613).

COMPOUND D trans-3-(1',1'-Dimethylheptyl)-6,6a,7,8,10,10a-hexahydro-1,6',9-trihydroxy-6,6-dimethyl-9H-dibenzo[b,d]pyran UV(EtOH) $\lambda_{max}$ 208, 225 (shoulder), and 275 nm ($\epsilon$ = 32000, 7300, and 130); ir (CHCl$_3$) 2.98 $\mu$ (OH); $^1$H NMR (CDCl$_3$) 6.34, 6.31 (2d, 1H each, J=2Hz, H$_2$ and H$_4$), 4.28 (broad s, 1H, H$_9$ equatorial), 3.74 (m, 1H, H$_6$'), 3.25 (broad d, 1H, J=15Hz, H$_{10}$ equatorial), 3.02–1.02 (33H) especially 2.96 (broad s, 1H, H$_{10a}$), 1.37 (s, 3H, 6$\beta$-CH$_3$), 1.19 (s, 6H, gem di-CH$_3$'s), 1.15 (d, 3H, J=6Hz, CH$_3$CH—OH), and 1.06 ppm (s, 3H, 6$\alpha$-CH$_3$); and exact mass determination gave m/e 390.2769 (calcd for C$_{24}$H$_{38}$O$_4$, 390.2770).

CHARACTERIZATION OF BACILLUS CEREUS NRRL B8172

This bacterium is classified as a strain of *Bacillus cereus* Frankland and Frankland. It is a large, spore-forming rod, averaging 4.7 $\mu$ × 1.6 $\mu$ and occurs in short chains. It is gram positive to gram variable and does not appear to be motile. Endospores are ellipsoidal and occur principally central to paracentral. Spores are produced readily within 18–24 hours on nutrient agar. Spores are 0.95 $\mu$ × 1.7 $\mu$. Sporangia are not swollen.

Colonies are slightly roughened, irregular, whitish-opaque, with undulate margins. The colony surface is dull, lacking a distinctive sheen.

The optimum temperature for growth is 30°. Growth occurs between 8° and 37° C. No growth occurs at 43° C.

In ammonium salts medium acid but no gas is produced from D-glucose and D-maltose. Neither acid nor gas is produced with L-arabinose, D-mannitol, and D-xylose. It does not produce either indole or H$_2$S. Gelatin is liquified rapidly within 24 hours, starch is hydrolyzed, peptonization of milk and acid production is slow (6days). The culture is catalase positive and produces acetyl methyl carbinol.

This culture differs from *Bacillus megaterium* by producing acetyl methyl carbinol and by not producing acid from mannitol.

As previously stated, substitution of other substrates according to Formula II above for ($\pm$)-trans-1-hydroxy-3-(1',1'-dimethylheptyl)-6,6-dimethyl-6,6a,7,8,10,10a-hexahydro-9H-dibenzo[b,d]pyran-9-one such as ($\pm$)-trans-3-(1',1'-dimethylheptyl)-6,6a,7,8,10,-10a-hexahydro-9H-dibenzo[b,d]pyran-1,9-diol, in the above fermentation yields the analogous four products: products having either a ketone or hydroxyl on the penultimate carbon of the side chain and either a ketone or hydroxyl at position 9 of the dibenzo[b,d]pyran ring. Similarly other organisms can be employed in place of *Bacillus cereus* NRRL B-8172 including such organisms as *Cumminghamella blakeselleeana, Cunninghamella elegans, Streptomyces cinnamonous, Mucor parasiticus,* etc.

The compounds of this invention are useful as analgesics. Their analgesic activity is shown by their ability to inhibit writhing in mice induced by the intraperitoneal injection of acetic acid. Inhibition of analgesic writhing is a standard laboratory test for analgesic activity. Estimated ED$_{50}$ (dose sufficient to inhibit 50 percent of the writhings) for the above compounds are as follows: Compound A, greater than 20 mg/kg; Compound B, 8.0 mg/kg; Compound C, 4.2 mg/kg; and Compound D, 2.0 mg/kg.

In addition to their utility as analgesics, some of the compounds of this invention are useful as intermediates for producing other compounds of the invention by reduction or oxidation. For example, compound A, a compound containing ketone functions at position 9 of the dibenzo[b,d]pyran ring system and on the penultimate carbon can be reduced by sodium borohydride to yield compound D which contains hydroxyls on the same two carbons. Similarly, compounds C and B can be reduced to yield compound D.

In employing the compounds of this invention as analgesics, the active drug can be mixed with a pharmaceutically acceptable diluent and the mixture filled into empty telescoping gelatin capsules so that each capsule contains one analgesic dose of the particular drug. A person requiring analgesia can then take from one to four of these capsules one to four times a day as prescribed by the physician. Other pharmaceutical formulations such as tablets, suspensions, and the like can also be employed.

We claim:

1. A compound of the formula

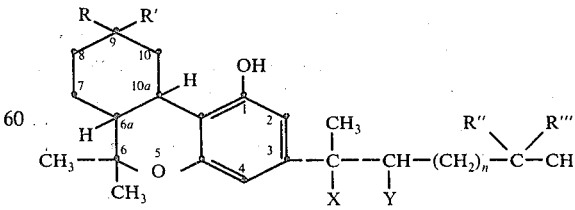

wherein X and Y are either both hydrogen or one is hydrogen and the other methyl;
wherein, when taken singly, one of the pair R and R' and one of the pair R" and R"' is H and the other is OH and, when taken together, the pair R and R' and the pair R" and R'" form the oxygen of a ketone group; and wherein n is 1, 2, 3 or 4.

2. A compound according to claim 1, said compound being (±)-trans-1-hydroxy-3-(1',1'-dimethylheptyl)-6,6-dimethyl-6,6a,7,8,10,10a-hexahydro-9H-dibenzo[b,d]-pyran-6',9-dione.

3. A compound according to claim 1, said compound being trans-1,6'-dihydroxy-3-(1',1'-dimethylheptyl)-6,6-dimethyl-6,6a,7,8,10,10a-hexahydro-9H-dibenzo[b,d]-pyran-9-one.

4. A compound according to claim 1, said compound being trans-1,9-dihydroxy-3-(1',1'-dimethylheptyl)-6,6-dimethyl-6,6a,7,8,10,10a-hexahydro-9H-dibenzo[b,d]-pyran-6'-one.

5. A compound according to claim 1, said compound being trans-1,6',9-trihydroxy-3-(1',1'-dimethylheptyl)-6,6-dimethyl-6,6a,7,8,10,10a-hexahydro-9H-dibenzo[b,d]pyran.

* * * * *